US012796954B2

(12) United States Patent
Lu et al.

(10) Patent No.: US 12,796,954 B2
(45) Date of Patent: Nov. 17, 2026

(54) DEVICES AND METHODS FOR ENDOLUMINAL POSITION DETECTION

(71) Applicant: Frond Medical Inc., Fremont, CA (US)

(72) Inventors: Xin Lu, Palo Alto, CA (US); Rose Monaghan, Los Gatos, CA (US); Albert Gee, Los Altos, CA (US); Michael J. Tierney, Pleasanton, CA (US); Raymond Chan, San Diego, CA (US)

(73) Assignee: Frond Medical Inc., Fremont, CA (US)

( * ) Notice: Subject to any disclaimer, the term of this patent is extended or adjusted under 35 U.S.C. 154(b) by 84 days.

(21) Appl. No.: 18/843,558

(22) PCT Filed: Mar. 10, 2023

(86) PCT No.: PCT/US2023/064168

§ 371 (c)(1),
(2) Date: Sep. 3, 2024

(87) PCT Pub. No.: WO2023/173108

PCT Pub. Date: Sep. 14, 2023

(65) Prior Publication Data

US 2025/0176852 A1 Jun. 5, 2025

Related U.S. Application Data

(60) Provisional application No. 63/269,215, filed on Mar. 11, 2022.

(51) Int. Cl.
*A61B 5/06* (2006.01)

(52) U.S. Cl.
CPC .................................... *A61B 5/065* (2013.01)

(58) Field of Classification Search
CPC ................................ A61B 5/065; A61B 5/064
See application file for complete search history.

(56) References Cited

U.S. PATENT DOCUMENTS 3,940,608 A 2/1976 Kissinger et al.
4,364,035 A 12/1982 Kirsch
(Continued)

FOREIGN PATENT DOCUMENTS

CN 101476902 A 7/2009
CN 112603537 A 4/2021
(Continued)

OTHER PUBLICATIONS

Notification of Transmittal of the International Search Report and the Written Opinion of the International Searching Authority, or the Declaration, issued for International Application No. PCT/US2021/072780, entitled “Methods and Systems for Body Lumen Medical Device Location,” mailed on Jul. 21, 2022.
(Continued)

*Primary Examiner* — Baisakhi Roy
(74) *Attorney, Agent, or Firm* — Hamilton, Brook, Smith & Reynolds, P.C.

(57) ABSTRACT

Systems and methods for measuring relative displacement between at least two flexible elongate instruments within a body lumen are provided. A system includes a first flexible elongate instrument comprising a plurality of spatial encoding markers and a second flexible elongate instrument comprising two detectors. Each detector comprises a single element sensor configured to obtain a signal from the spatial encoding markers. The single element sensor of one of the two detectors is offset from the single element sensor of the other of the two detectors. The first and second flexible elongate instruments are configured for relative movement within a body lumen. The system further includes a controller configured to measure relative displacement of the first and second flexible elongate instruments based on the signals obtained from the two detectors and a detected offset of the obtained signals.

32 Claims, 7 Drawing Sheets

(56) References Cited

U.S. PATENT DOCUMENTS

| | | | |
|---|---|---|---|
| 4,582,061 | A | 4/1986 | Fry |
| 4,624,570 | A | 11/1986 | Bertollini |
| 4,631,519 | A | 12/1986 | Johnston |
| 4,711,578 | A | 12/1987 | Chaimowicz |
| 4,794,931 | A | 1/1989 | Yock |
| 4,841,977 | A | 6/1989 | Griffith et al. |
| 4,951,677 | A | 8/1990 | Crowley et al. |
| 5,000,185 | A | 3/1991 | Yock |
| 5,073,027 | A | 12/1991 | Krohn et al. |
| 5,095,911 | A | 3/1992 | Pomeranz |
| 5,135,486 | A | 8/1992 | Eberle et al. |
| 5,176,141 | A | 1/1993 | Bom et al. |
| 5,240,003 | A | 8/1993 | Lancee et al. |
| 5,243,988 | A | 9/1993 | Sieben et al. |
| 5,313,949 | A | 5/1994 | Yock |
| 5,321,501 | A | 6/1994 | Swanson et al. |
| 5,353,798 | A | 10/1994 | Sieben |
| 5,373,845 | A | 12/1994 | Gardineer et al. |
| 5,373,849 | A | 12/1994 | Maroney et al. |
| 5,375,602 | A | 12/1994 | Lancee et al. |
| 5,409,004 | A | 4/1995 | Sloan |
| 5,453,575 | A | 9/1995 | O'Donnell et al. |
| 5,709,661 | A | 1/1998 | Van et al. |
| 6,275,724 | B1 | 8/2001 | Dickinson et al. |
| 6,332,089 | B1 | 12/2001 | Acker et al. |
| 6,428,512 | B1 | 8/2002 | Anderson et al. |
| 6,690,964 | B2 | 2/2004 | Bieger et al. |
| 6,999,811 | B2 | 2/2006 | Koppe et al. |
| 7,033,325 | B1 | 4/2006 | Sullivan |
| 7,474,407 | B2 | 1/2009 | Gutin |
| 7,929,148 | B2 | 4/2011 | Kemp |
| 8,108,030 | B2 | 1/2012 | Castella et al. |
| 8,125,648 | B2 | 2/2012 | Milner et al. |
| 8,531,676 | B2 | 9/2013 | Condit et al. |
| 8,540,648 | B2 | 9/2013 | Uihlein |
| 8,809,764 | B2 | 8/2014 | Kato |
| 8,989,849 | B2 | 3/2015 | Milner et al. |
| 9,031,314 | B2 | 5/2015 | Clausen et al. |
| 9,046,339 | B2 | 6/2015 | Blatter et al. |
| 9,393,079 | B2 | 7/2016 | Weese et al. |
| 9,417,057 | B2 | 8/2016 | 'T et al. |
| 9,730,613 | B2 | 8/2017 | Stigall et al. |
| 10,219,780 | B2 | 3/2019 | Castella et al. |
| 10,737,070 | B2 | 8/2020 | Richer et al. |
| 2002/0042582 | A1 | 4/2002 | Vrba et al. |
| 2003/0187369 | A1 | 10/2003 | Lewis et al. |
| 2004/0133129 | A1 | 7/2004 | Harari et al. |
| 2005/0054910 | A1 | 3/2005 | Tremblay et al. |
| 2006/0173381 | A1 * | 8/2006 | Eck ....................... A61M 25/00 600/585 |
| 2007/0135803 | A1 | 6/2007 | Belson |
| 2007/0197891 | A1 * | 8/2007 | Shachar ................... A61B 5/33 600/374 |
| 2008/0146942 | A1 | 6/2008 | Dala-Krishna |
| 2008/0262473 | A1 * | 10/2008 | Kornblau ................. A61B 5/06 604/529 |
| 2012/0226227 | A1 | 9/2012 | Weitzner et al. |
| 2013/0137963 | A1 | 5/2013 | Olson |
| 2015/0182190 | A1 | 7/2015 | Hiltner et al. |
| 2015/0265367 | A1 | 9/2015 | Gruhler |
| 2015/0282890 | A1 | 10/2015 | Cohen et al. |
| 2015/0335867 | A1 * | 11/2015 | Elton .................. A61M 25/104 604/103.1 |
| 2017/0007333 | A1 | 1/2017 | Sanz et al. |
| 2017/0332999 | A1 | 11/2017 | Coolidge et al. |
| 2018/0014886 | A1 | 1/2018 | Flexman et al. |
| 2018/0289430 | A1 | 10/2018 | Kahya et al. |
| 2020/0155239 | A1 | 5/2020 | West et al. |
| 2020/0367786 | A1 | 11/2020 | Govari et al. |
| 2022/0175269 | A1 | 6/2022 | Lu et al. |

FOREIGN PATENT DOCUMENTS

| | | | |
|---|---|---|---|
| DE | 19750698 | A1 | 5/1998 |
| JP | 2014-128649 | A | 7/2014 |
| JP | 2017-518786 | A | 7/2017 |
| JP | 2017-131348 | A | 8/2017 |
| WO | 2006/043276 | A2 | 4/2006 |
| WO | 2009/112048 | A1 | 9/2009 |
| WO | 2014/060621 | A1 | 4/2014 |
| WO | 2014/102599 | A1 | 7/2014 |
| WO | 2015/101747 | A1 | 7/2015 |
| WO | 2018/051111 | A1 | 3/2018 |
| WO | 2020/234668 | A1 | 11/2020 |
| WO | 2022126101 | A2 | 6/2022 |

OTHER PUBLICATIONS

International Search Report and Written Opinion for Int'l Application No. PCT/US2023/064168, entitled "Devices and Methods for Endoluminal Position Detection," consisting of 11 pages. Date of Mailing Jun. 23, 2023.

* cited by examiner

DEVICES AND METHODS FOR ENDOLUMINAL POSITION DETECTION

RELATED APPLICATION

This application is the U.S. National Stage of International Application No. PCT/US2023/064168, filed Mar. 10, 2023, which designates the U.S., published in English, and claims the benefit of U.S. Provisional Application No. 63/269,215, filed on Mar. 11, 2022. The entire teachings of the above application are incorporated herein by reference.

BACKGROUND

Intracoronary imaging is often used to accurately measure vessel and stenosis dimensions, assess vessel integrity, characterize lesion morphology and aide in body lumen procedures, including percutaneous coronary intervention (PCI) procedures. The frequency of complex percutaneous coronary interventions has steadily increased in recent years due to clinical benefits provided by the interventions, which can increase the life expectancy and quality of life for patients suffering from endovascular neurosurgical, cardiovascular, and peripheral artery diseases. Various diagnostic and therapeutic medical devices (e.g., guidewires, balloons, atherectomy, lithotripsy, stents, imaging and physiology diagnostic modalities, X-ray angiography, and fluoroscopy) enable radiologists, cardiologists, and vascular specialists to visualize a patient's intra-vasculature to guide treatment decisions and to perform intervention procedures. Often, X-ray fluoroscopy with contrast injection is used to guide physicians to position devices (e.g., stents, guidewires, and balloons) toward targeted lesion locations along a guidewire within the endo-vasculature.

In a PCI procedure, vascular access is typically gained through an arterial entry point, such as the radial, brachial, or femoral artery, or through a venous puncture. From the entry point, a physician can access the vasculature of organs such as heart, lungs, kidneys, and brain by advancing a guidewire into the patient until a distal end of the guidewire crosses, for example, a lesion to be treated. After the guidewire position is finalized and situated such that it is viewable on an angiographic image, a desired therapeutic and/or diagnostic device is mounted on a proximal end of the guidewire. The therapeutic and/or diagnostic device is then advanced towards the distal end to the feature of interest.

Depending upon the clinical situation, imaging and/or physiological probes, such as Intravascular Ultrasound (IVUS), Optical coherence tomography (OCT) and Fractional Flow Reserve (FFR) devices, can be used for pre-intervention assessment, such as for determining lesion location, lesion dimension, plaque morphology, and coronary pressure at an area of interest. Endoluminal diagnostic modalities, such as IVUS, OCT, and FFR, which are able to generate more detailed vessel lumen information than that which can be obtained from X-ray imaging alone, are widely used for minimally invasive PCI procedures.

Endoluminal device guidance generally requires a live display of the device's movement inside of a body lumen. The methods currently available for guidance and positioning are based on real-time X-ray angiographic imaging, such that both a blood vessel's lumen path and the device inside of the lumen are continuously visible during the procedure. X-ray imaging for blood vessel diagnosis and device guidance emits X-rays at many frames per second and often requires contrast fluid injection, which allows for visualization of the vessel to help clinicians locate and position medical instruments. This practice results in high radiation exposure to both patients and clinicians, as well as the delivery of large volumes of contrast agents to patients, which are harmful to the kidneys.

There exists a need for improved systems and methods for providing endoluminal device guidance and locating medical devices within a body lumen.

SUMMARY

Systems and methods are provided that can enable improved position detection, including orientation and direction detection, of flexible elongate instruments disposed within a body lumen.

A system for measuring relative displacement between at least two flexible elongate instruments within a body lumen includes a first flexible elongate instrument comprising a plurality of spatial encoding markers and a second flexible elongate instrument comprising two detectors. Each detector includes a single element sensor configured to obtain a signal from the spatial encoding markers. The single element sensor of one of the two detectors is offset from the single element sensor of the other of the two detectors. The first and second flexible elongate instruments are configured for relative movement within a body lumen. The system further includes a controller configured to measure relative displacement of the first and second flexible elongate instruments based on the signals obtained from the two detectors and a detected offset of the obtained signals.

The sensor offset can be a spatial offset in at least one direction, for example, a longitudinal offset, an angular offset, or a combination thereof. For a longitudinal offset, for example, one sensor is disposed at a greater distance from a distal end of the device than the other sensor. This can enable one sensor to lead the other during travel of the instrument. For an angular offset, for example, one sensor can be disposed at a different angle with respect to the first flexible elongate instrument than that of the other, such that each sensor is capable of viewing a different circumferential portion of the first flexible elongate instrument. The offset between the single element sensors can be fixed. The controller can be further configured to determine a relative direction of movement between the first and second flexible elongate instruments based on the detected offset, a relative change in orientation between the first and second flexible elongate instruments based on the detected offset, or a combination thereof. The spatial encoding markers can comprise a pattern that varies about a circumference of the first flexible elongate instrument to enable detection of changes in orientation and/or rotation.

A position of the first flexible elongate instrument can be fixed in a reference coordinate frame, and the controller can be further configured to determine an absolute position of the second flexible elongate instrument in the reference coordinate frame based on the detected offset of the signals obtained from the two detectors.

The controller can be further configured to translate the obtained signals to code characters and determine an absolute position of one of the first and second flexible elongate instruments based on the code characters. Alternatively, or in addition, the controller can be further configured to determine an incremental change in position between the first and second flexible elongate instruments based on at least one of amplitude, frequency, phase, and timing variations between the obtained signals. The determined incremental change in position can be translated to an absolute position of one of the first and second flexible elongate instruments based on the detected offset of the signals obtained from the two detectors. Typically, one of the first and second flexible elongate instruments is fixed within a coordinate frame of reference. Thus, the system can provide for a detected change in position and/or orientation of the second flexible elongate relative to the first flexible elongate instrument and determine a position and/or orientation of the second flexible elongate instrument in the coordinate frame of reference.

The detectors can be optical detectors, and each single element sensor can be a single element light sensor. Alternatively, the detectors can be magnetic field detectors, and each single element sensor can be a Hall effect sensor.

A stimulation energy source (e.g., a light source) associated with at least one of the two detectors can be configured to deliver pulsed energy or continuous energy. A stimulation energy source can be associated with each of the two detectors, and a stimulation energy associated with one source can vary with respect to that of the other source in at least one of phase, timing, amplitude, and frequency.

The system can further include a localization sensor or marker for spatial alignment of at least a subset of the encoding markers to a position defined in both a coordinate frame of reference of the system and a coordinate frame of reference of another modality. The localization marker can be an imaging marker.

A multi-modality localization method includes aligning one of the first and second flexible elongated instruments relative to a localization sensor or marker and registering a position and orientation of the one of the first and second flexible elongated instruments based on a detected position and orientation of the localization sensor or marker in both a coordinate frame of reference of the system and a coordinate frame of reference of another modality.

The method can further include updating a spatial measurement obtained from the other modality based on the measured relative displacement of the first and second flexible elongate instruments by the system.

A method of measuring relative displacement between at least two flexible elongate instruments within a body lumen includes measuring relative displacement between a first flexible elongate instrument and a second flexible elongate instrument based on signals obtained from each of two detectors of the second flexible elongate instrument and a detected offset of the obtained signals. The first flexible elongate instrument includes a plurality of spatial encoding markers. The second flexible elongate instrument includes the two detectors, each detector comprising a single element sensor configured to obtain a signal from the spatial encoding markers. The single element sensor of one of the two detectors is offset from the single element sensor of the other of the two detectors. The first and second flexible elongate instruments are configured for relative movement within a body lumen.

The method can further include determining a relative direction of movement between the first and second flexible elongate instruments based on the detected offset, determining a relative change in orientation between the first and second flexible elongate instruments based on the detected offset, or a combination thereof.

A position of the first flexible elongate instrument can be fixed in a reference coordinate frame, and the method can further include determining an absolute position of the second flexible elongate instrument in the reference coordinate frame based on the detected offset of the signals obtained from the two detectors.

The method can further include translating the obtained signals to code characters and determining an absolute position of one of the first and second flexible elongate instruments based on the code characters.

The method can further include determining an incremental change in position between the first and second flexible elongate instruments based on at least one of amplitude, frequency, phase, and timing variations between the obtained signals. The determined incremental change in position can be translated to an absolute position of one of the first and second flexible elongate instruments based on the detected offset of the signals obtained from the two detectors.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 1A is a schematic of a cross-section of a catheter comprising two detectors having an angular offset with respect to a guidewire lumen. FIG. 1B is a schematic of the two detectors having a longitudinal offset. FIG. 1C is a schematic of system components with an encoded guidewire disposed within the guidewire lumen.

FIG. 7A is a cross-sectional view of the catheter with the two detectors. FIG. 7B is a schematic of the two detectors and a light source.

FIG. 9A illustrates an example detector with an array-type sensor. FIG. 9B illustrates an example of a detector with a single-element sensor. FIG. 9C illustrates another example of a detector with a single-element sensor.

DETAILED DESCRIPTION

Examples of systems and methods providing for position detection of endoluminal instruments are described in International Pub. No. WO 2022/126101, titled "Methods and Systems for Body Lumen Medical Device Location," the entire teachings of which are incorporated herein by reference. Among such systems and methods are optical-based linear encoding instruments. For example, such systems can include an optical sensor and optical fiber built into or onto a flexible elongate instrument, such as a guidewire or a catheter-based device, for insertion into a body lumen. Encodings located on or in another flexible elongate instrument, such as a diagnostic or therapeutic-delivery device, can be detected by the optical sensor, thereby providing for relative position detection of the instruments within the body lumen. Such systems and methods can advantageously provide for a profile small enough to be positioned within, for example, blood vessels, while enabling accurate determination of an endoluminal diagnostic or therapeutic device's location within the body lumen.

A description of example embodiments follows.

Improvements to the systems and methods described in Intl. Pub. No. WO 2022/126101 are provided. The provided systems and methods can enable improved position detection, including orientation and direction detection, of flexible elongate instruments disposed within a body lumen.

Figure 1A:
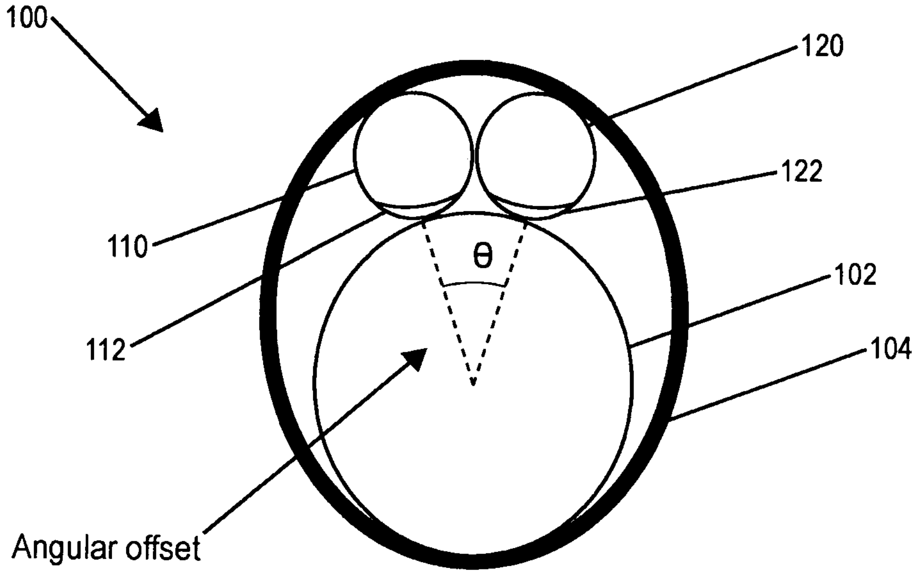
FIGS. 1A-1C are schematics of an example system for measuring relative displacement of flexible elongate instruments within a body lumen.
Figure 1B:
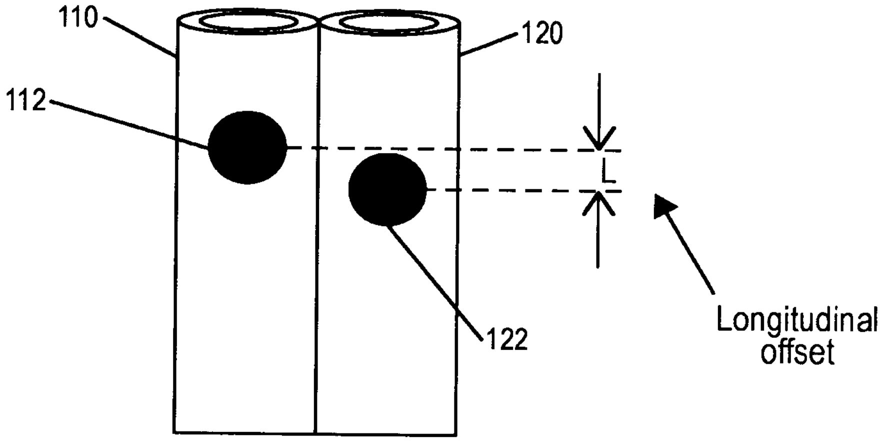
Figure 1C:
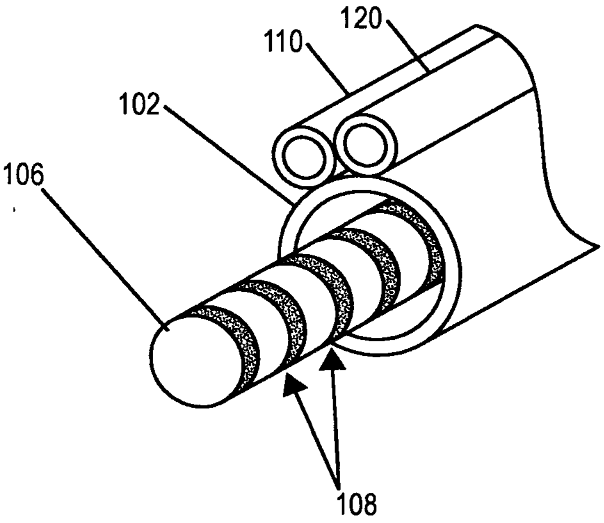

An example system for measuring relative displacement between at least two flexible elongate instruments within a body lumen is shown in FIGS. 1A-1C. The system 100 includes a first flexible elongate instrument 106 (e.g., a guidewire, FIG. 1C) and a second flexible elongate instrument 104 (e.g., a catheter, FIG. 1A, which can be a microcatheter providing for diagnostic or therapeutic device access). The first flexible elongate instrument 106 includes a plurality of spatial encoding markers 108 (e.g., markers encoding at least one of displacement, position, and orientation). The second flexible elongate instrument 104 includes two detectors 110, 120 (e.g., optical detectors).

As illustrated in FIGS. 1A-1C, the spatial encoding markers 108 are included on or in a guidewire of the system, and detectors 110, 120 are included on or in a catheter of the system. However, it should be understood that encoding markers can alternatively be included on or in a catheter, and detectors can alternatively be included on or in a guidewire. For example, a guidewire can include two integrated optical fibers, and encodings disposed on a microcatheter can be detected by optical windows disposed on the guidewire as the microcatheter travels over the guidewire. Optionally, a guidewire catheter 102 is included, with the guidewire 106 disposed within the guidewire catheter 102 as one of the instruments is displaced relative to the other. The guidewire catheter can be of a material that is transparent to a stimulation energy used for detection (e.g., a clear tube for optical detection, a material permitting magnetic detection, etc.)

Each detector 110, 120 can be, for example, an optical detector. Each optical detector 110, 120 can include a single element light sensor 112, 122 configured to obtain a signal from the displacement encoding markers 108. Each optical detector 110, 120 can be, for example, an optical fiber or a tube comprising an optical fiber. The detectors 110, 120 can be fixed relative to one another such that there is a fixed, spatial offset of the two sensors 112, 122. The offset can be a longitudinal offset (L), as shown in FIG. 1B, and/or an angular offset (θ), as shown in FIG. 1A. A longitudinal offset can provide for a determination as to a relative direction of movement between the first and second flexible elongate instruments. An angular offset can provide for a determination as to a relative change in orientation between the first and second flexible elongate instruments. Thus, the system can provide for not only detection of linear displacement between the instruments, but also rotational displacement between the instruments, as well as provide for detection of a direction of displacement in either or both cases.

Figure 2:
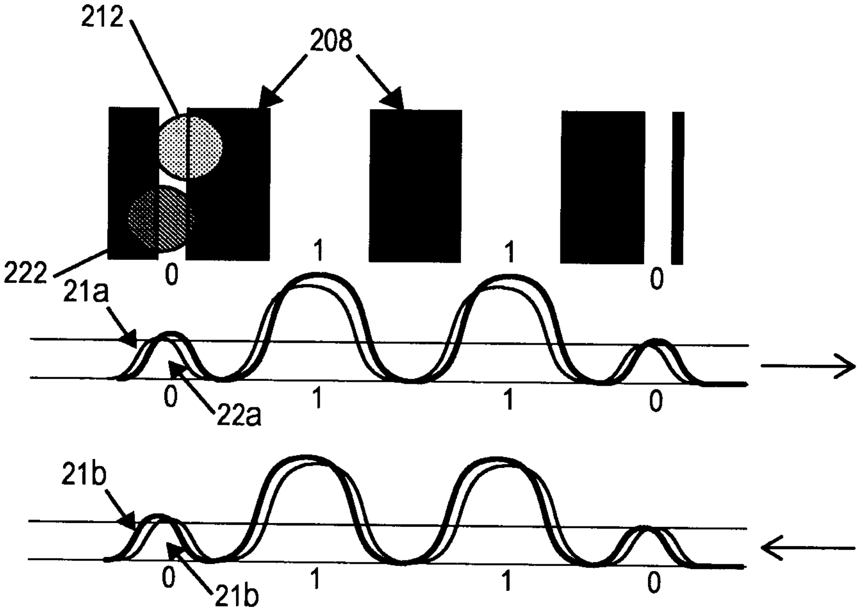
FIG. 2 is a diagram illustrating example detection signals obtained from an encoded guidewire using a system comprising two detectors, providing for detection of directional movement.

A diagram illustrating example operation of the system 100 is shown in FIG. 2. The example is described with respect to the detectors being optical detectors and the sensors being, for example, apertures in an optical fiber through which light reflected from the encoding markers may enter the detector. However, it should be understood that other types of detectors can be used, including the additional examples further described herein.

As illustrated in FIG. 2, encoding markers 208 are markers having high and low light-reflectance, which can provide for binary (e.g., 0,1) encodings. Such binary markings can be further organized to provide for multi-bit encoding along a length of a guidewire to provide for absolute position detection of a catheter as it travels along the guidewire. For example, a 4-bit binary encoding can provide for detection of up to sixteen unique positions along the guidewire. Where a position of the guidewire has been fixed within another frame of reference, for example, an imaging frame of reference (e.g., an x-ray image), a position of the catheter can be precisely correlated to the imaging frame of reference based on the detected encodings. This can enable more precise positioning of the catheter for a diagnostic or therapeutic procedure, particularly where reference to another imaging modality is needed or desired to provide for proper positioning.

Methods and systems that provide for absolute position encoding and correlation to other frames of reference are further described in Intl. Pub. No. WO 2022/126101. Such systems and methods make use of an optical detector integrated within either a guidewire, a catheter, or other endoluminal device, with such a detector being capable of detecting encodings disposed on the other of the two devices. Such an arrangement can provide for significant improvements over conventional systems, as further described in Intl. Pub. No. WO 2022/126101.

With endoluminal procedures, such as percutaneous coronary intervention (PCI) procedures, inconsistencies and minor variations in the advancement or retraction of an instrument can occur. It can be desirable to provide for the detection of a direction of movement, which may be difficult where a single optical detector is utilized. For example, if a detector associated with a catheter delivering a therapeutic device is moving in a distal direction and has paused over an area of low reflectance (e.g., a "1"), and if there is a brief period of proximal movement before distal movement is resumed (as can occur where a physician is manually advancing an instrument), it may not be possible to distinguish whether a next-detected area of high reflectance (e.g., a "0") is indicative of the device having moved in the proximal or distal direction, and disruptions in code detections can occur.

Returning to FIG. 2, a longitudinal offset between apertures 212, 222 of two optical detectors results in a phase shift of the detected signals. For example, when moving in a direction from left to right, a signal 21*a*, as detected from aperture 212 (light grey), will precede a signal 22*a* detected from aperture 222 (dark grey). Similarly, when moving in a direction from right to left, a signal 22*b*, as detected from aperture 222 (dark grey), will precede a signal 21*b*, as detected from aperture 212 (light grey). The dimensions of the longitudinal offset between the two apertures 212, 222 can be known, thereby enabling a comparison of the signals to distinguish direction and, optionally, to distinguish between varying widths of areas of high and low reflectance, as shown in FIG. 2.

Figure 3:
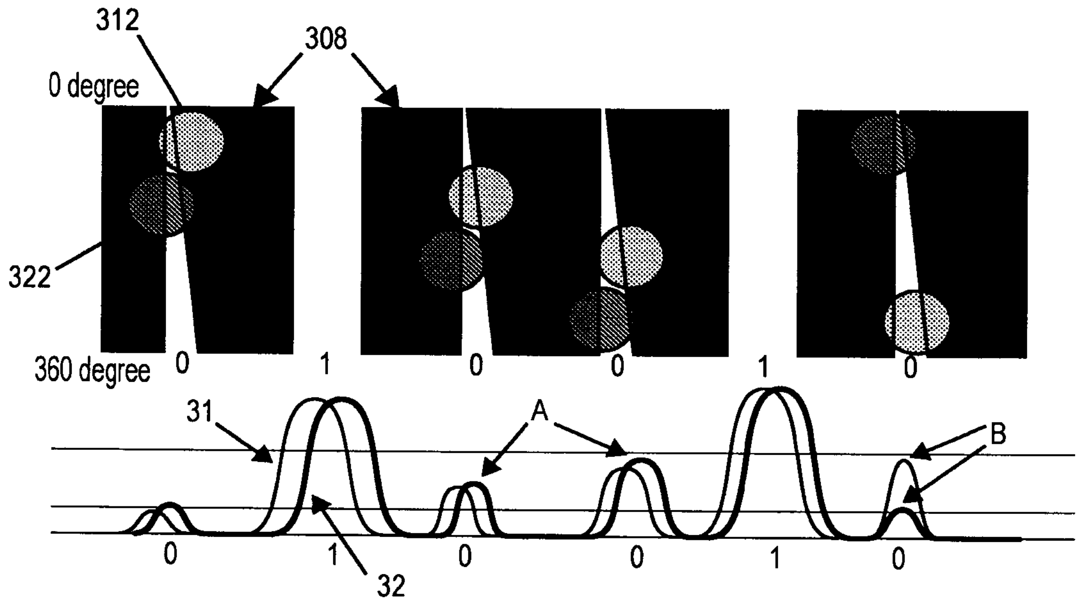
FIG. 3 is a diagram illustrating example detection signals obtained from an encoded guidewire using a system comprising two detectors, providing for detection of rotational movement.

A diagram illustrating another example operation of the system 100 is shown in FIG. 3, where an angular offset exists between apertures 312, 322 of the two optical detectors. An angular offset, together with an encoding pattern 308 that varies about a circumference of the guidewire, can provide for detection of rotational and/or orientation changes between the instruments. For example, due to the varying widths of areas of high and low reflectance at a given position, a signal 31, as detected from the aperture 312 (light grey), can vary in amplitude with that of a signal 32, as detected from the aperture 322 (dark grey). The dimensions of the angular offset between the two apertures 312, 322 can be known, enabling a comparison of the signals to distinguish changes in orientation between the instruments.

While encodings having varying widths are shown in FIGS. 2 and 3, other measurable patterns can be used. For example, encodings of the first flexible elongate instrument can include patterns having one or more features (e.g., code bars of a width, color, engraved depth, and/or density) that vary as a function of position about a circumference of the instrument and/or along a length of the instrument.

The inclusion of two detectors (e.g., detectors 110, 120) in a system can provide for more robust signal detection, which can confer more accurate conversion to code characters. The detector can also be used with simpler encoding (e.g., two widths, colors, or depths of encoding markers), thereby reducing complexity of decoding while still providing for directional information to be obtained from the offset in signals from the two detectors.

Orientation and direction detection can provide for improved mapping with other modalities. For example, the inclusion of at least two sensors in the system can provide for additional degrees of measurement, such as degrees of rotation in a system coordinate frame of reference. Measured degrees of rotation can be considered in addition to other position coordinates (e.g., x-, y-, z-coordinates in a 3D space) to provide for a more precise measurement of a location of a device in a body lumen.

In conventional systems, displacement of a diagnostic device (e.g., IVUS, FFR) is actuated by a motor drive unit placed outside of a patient, and the tracking of displacement also occurs outside of the body lumen. There can be a large discrepancy between the measured displacement of a diagnostic device as estimated by a motor drive unit and an actual sensor displacement inside of the body lumen. Discrepancies can result due to diameter differences between a moving medical instrument and a guide catheter and the effects of inherent vessel elasticity. Furthermore, precise length measurement of vessel features can be needed to properly choose a size of a treatment device (e.g., an angioplasty balloon, cutting balloon, and stents). While constant X-ray angiography can be used to track the movement of a diagnostic sensor displacement, this method exposes the patient to undesirable amounts of contrast solution and both the patient and operator to high levels of X-ray radiation.

Once a vessel endoluminal diagnostic procedure has been performed that provides more detailed information about the vessel lumen than from an X-ray angiography, a treatment decision is often made based on the endoluminal diagnostic information. The treatment decision can be based on a precise location within the vessel of the lesion. Typically, subsequent treatment procedures are guided by X-ray imaging alone. Even with the benefit of vessel location correlation between an X-ray image and endoluminal diagnostic images, it can be desirable that the location of a treatment device moving inside of a vessel lumen be visualized directly in real-time or about real-time on an endoluminal diagnostic image previously generated to help position the diagnostic and/or therapeutic device at a vessel location of interest that has been identified on the diagnostic image. In some instances, a clinician can use features that are visible on both an X-ray and endoluminal diagnostic scan, such as a vessel branch or severe narrowing, to help identify corresponding locations so as to attempt to improve the measurement accuracy of a guided therapeutic and/or diagnostic device during a PCI.

Thus, it can be advantageous to acquire instrument-position tracking data using sensors disposed at the location of interest within the body lumen, as opposed to relying on displacement measurements obtained from sensors disposed outside the body. With a "single-element sensor," a detector (or at least a sensing portion thereof) can be made small enough to be constructed into an endoluminal device.

As used herein, the term "single-element sensor" refers to a non-array sensor. A "single-element sensor" can be a single pixel sensor or a multiple pixel sensor that provides for a single output signal. Examples of single element sensors and optical detectors comprising single element sensors are further described in Intl. App. No. PCT/US2021/072780. A single-element sensor can be, for example, a single-pixel light sensor or a Hall effect plate.

Figure 9A:
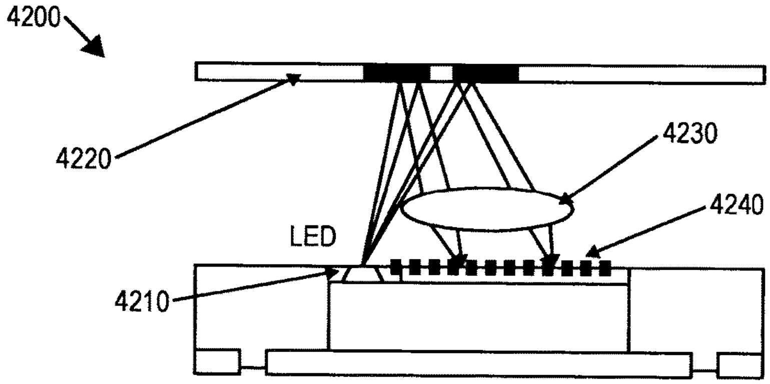
FIG. 9A (PRIOR ART)
FIGS. 9A-9C are schematics of prior art optical detector configurations.
Figure 9B:
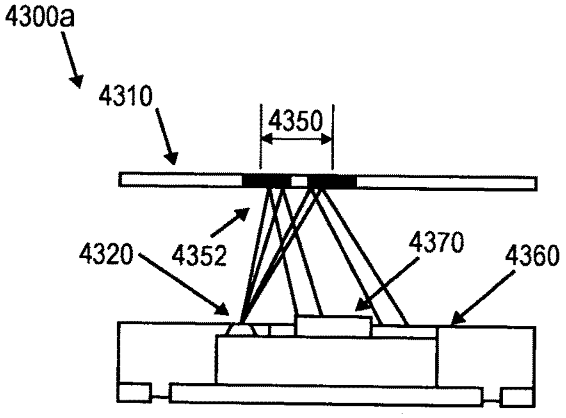
FIG. 9B (PRIOR ART)
Figure 9C:
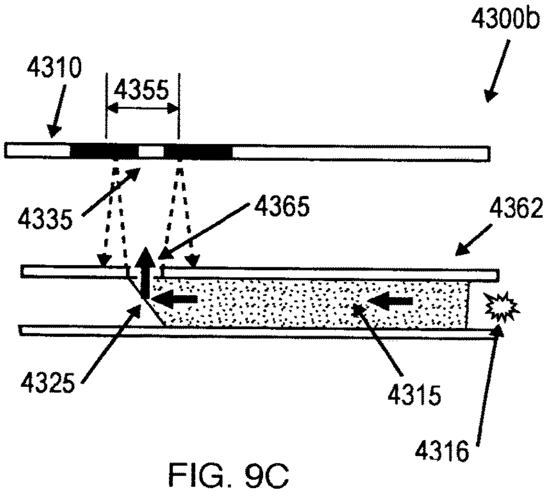
FIG. 9C (PRIOR ART)

Examples of single-element sensors for use in the provided systems, and comparison to an array type sensor, are shown in FIGS. 9A-9C. FIG. 9A illustrates a commonly used, prior art, array-type sensor 4200 for absolute position encoding. A light source 4210 illuminates the code track 4220. Light from the light source 4210 is reflected off the code track, passes through an optical lens 4230, and is focused on an array-type sensor 4240. The array sensor 4240 includes several sensing elements, or pixels. Common array-type sensors can be constructed of CCD sensors, or CMOS sensors, for example. The array can also be either a linear array oriented in the direction of movement, or a two-dimensional array that can include thousands of pixels. Spacing information of the code lines are captured by the array sensor and conveyed to computer processor.

FIGS. 9B-C illustrate two prior art examples of systems 4300*a*, 4300*b* with single sensing element sensors. As illustrated in FIG. 9B, a code track 4310 is illuminated by a light source 4320. Any type of light source can be used for illumination. The light is projected onto the code track 4310, illuminating a finite illuminated area 4352 that has a finite width 4350 in the direction of movement between the code track 4310 and the detector 4360. The reflected light from code track 4310 is captured by sensor 4370, which is a single-sensing-element sensor, also referred to as a single-pixel sensor. Optionally, multiple sensing elements or pixels can be used, but each sensing element or pixel may then not provide a separate output; rather sensing can be combined into a single output, or a single channel, such that the position information of each individual pixel is not captured.

As illustrated in FIG. 9C, a detector 4362 includes an optical fiber 4315 that transfers light from a light source 4316. A reflective surface 4325 is illustrated as a 45-degree polished end surface of the fiber 4315 having a reflective coating. The coating can be made from a number of materials, such as, for example, aluminum, silver, chrome, gold, platinum, etc., which can be applied to the surface via, for example, vacuum deposition. The light is reflected by the reflective surface 4325, exits a window 4365, and illuminates a finite illuminated area 4335 on the code track 4310. The finite area 4335 has a finite width 4355 in the direction of movement. A portion of the reflected light from code track 4310 re-enters the window 4365 and follows the optical fiber to a light sensor. The optical fiber can transmit light from a light source to illuminate the code track and transmit the reflected light from the code track to a light sensor.

Figure 6:
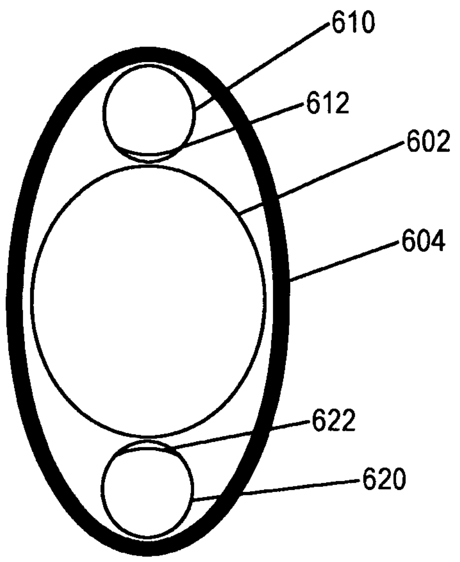
FIG. 6 is a schematic of an example configuration of two detectors within a catheter.

Detectors (e.g., detectors 110, 120) can be arranged within a catheter 104 (e.g., catheter 104) in varying configurations with respect to one another and with respect to a light source (or other stimulation energy source). As illustrated in FIG. 1A, the detectors 110, 120 are disposed adjacent to one another and can be "active" detectors (i.e., each detector has an associated light source, or other stimulation energy source). Alternatively, as illustrated in FIG. 6, detectors 610, 620 can be disposed within a catheter 604 such that the detectors 610, 620 are on opposing sides of a guidewire catheter 602. The sensors 612, 622 of each detector can be disposed to detect encodings on opposing sides of a guidewire (not shown) disposed in the guidewire catheter 602.

Figure 7A:
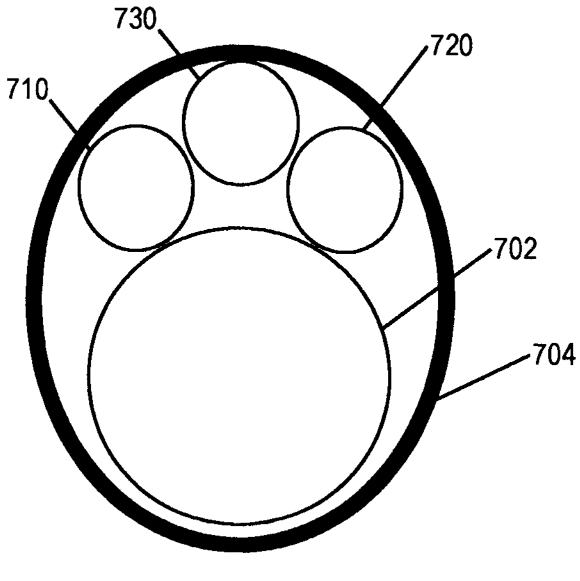
FIGS. 7A-7B are schematics of another example configuration of two detectors within a catheter and with a shared light source.
Figure 7B:
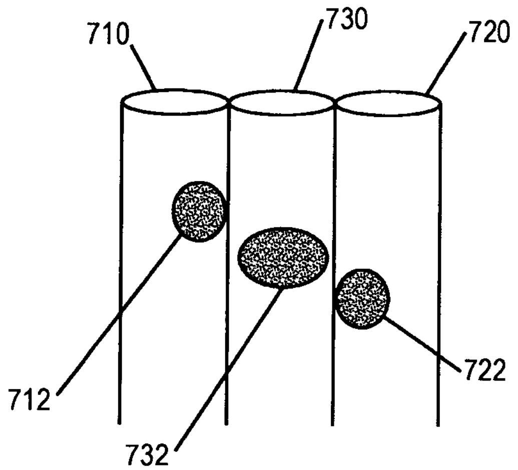

In another example, shown in FIGS. 7A-7B, the detectors 710, 720 can be "passive" detectors, which make use of a shared light source 730 disposed within the catheter 704. The shared light source 730 can illuminate a guidewire (not shown) in the guidewire catheter 702. For example, as shown in FIG. 7B, an aperture 732 associated with the light source 730 can be disposed between an offset of apertures 712, 722 of the detectors 710, 720, providing for illumination of the encoding markers for detection by each detector.

Figure 4:
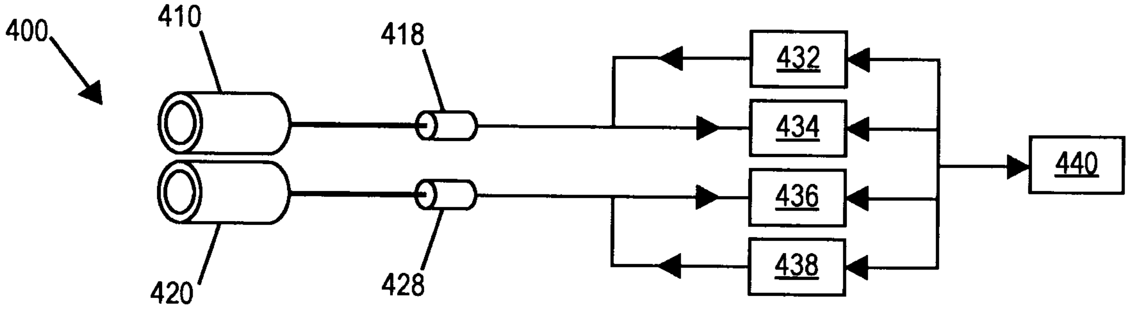
FIG. 4 is a schematic of an example of a system having two optical detectors, each with a dedicated light source, and optical couplings that can be disposed outside a body.
Figure 5:
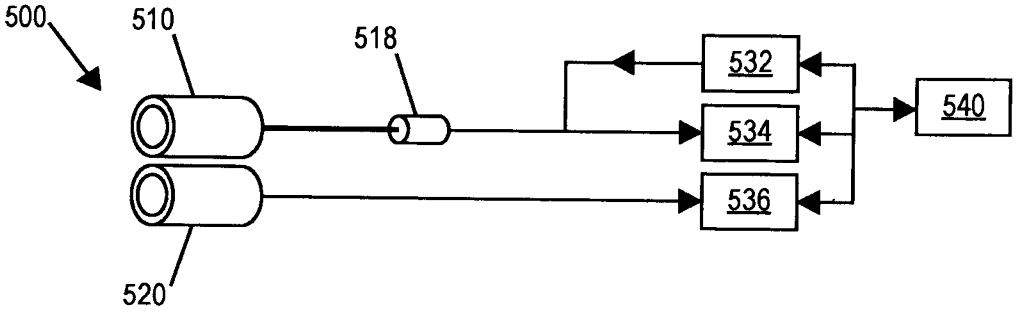
FIG. 5 is a schematic of another example of a system having two optical detectors with a shared light source.

Additional example configurations are shown in FIGS. 4 and 5. A system 400 includes two detectors 410, 420, each of which can comprise an optical fiber tube with an aperture configured to enable the emission of light for illumination of a code track on a guidewire and detection of light reflected from the code track. To provide for a minimal device profile, optical connectors 418, 428 can be provided at a location outside the body to couple the optical fibers of detectors 410, 420 to respective light sources 432, 438 and respective light sensors 434, 436. A controller 440 can be configured to operate the light sources 432, 438 and receive signals from the sensors 434, 436.

Optionally, a single light source can instead be included. A system 500 includes two detectors 510, 520. One of the detectors 510 is coupled to an optical connector 518 to provide for connection to a light source 532 that may be shared with the other of the detectors 520. Each detector is coupled to a respective optical sensor 534, 536. A controller 540 can be configured to operate the light source 532 and receive signals from the sensors 534, 536.

One or more light sources of the system can be configured to provide pulsed light. For example, pulses applied to each of the two optical detectors (e.g., detectors 410, 420) can be provided with a phase shift so as to avoid light contamination from one detector to the other. A 180° phase shift can be applied such that a light source associated with one detector is ON while a light source associated with the other detector is OFF. Alternatively, or in addition, optical detectors can be disposed on opposing sides of the first flexible elongate instrument (see, e.g., FIG. 6) to reduce or avoid light contamination from each detector.

A stimulation energy (e.g., light) associated with one source can vary with respect to stimulation energy associated with the other source in at least one of phase, timing, amplitude, and frequency.

Optionally, one light source can be provided for use with each of the two optical detectors (e.g., detectors 510, 520). The light source can be positioned common to each of the detectors (see, e.g., FIGS. 7A-B), and the detectors can be passive detectors.

A controller (e.g., controller 440, 540) can be configured to measure relative displacement of the first and second flexible elongate instruments (e.g., guidewire 106 and catheter 104) based on the signals obtained from the two detectors and a detected offset of the obtained signals (e.g., as shown in FIGS. 2 and 3). The measured relative displacement can be used by the controller to determine an absolute position of the second flexible elongate instrument (e.g., based on translation of detected code characters to position data and accounting for detected changes in direction/orientation). For example, where a position of the first flexible elongate instrument is fixed in a coordinate frame of reference (see, e.g., FIG. 8) and known, the absolute position of the second flexible elongate instrument can be determined.

Alternatively, or in addition, an incremental position change between the first and second flexible elongate instruments can be determined by the controller. The incremental position change can be based on at least one of amplitude, frequency, phase, and timing variations between the obtained signals. A determined incremental position change can be translated to a determined absolute position to enhance accuracy of measuring a position of one of the instruments during a procedure.

Figure 8:
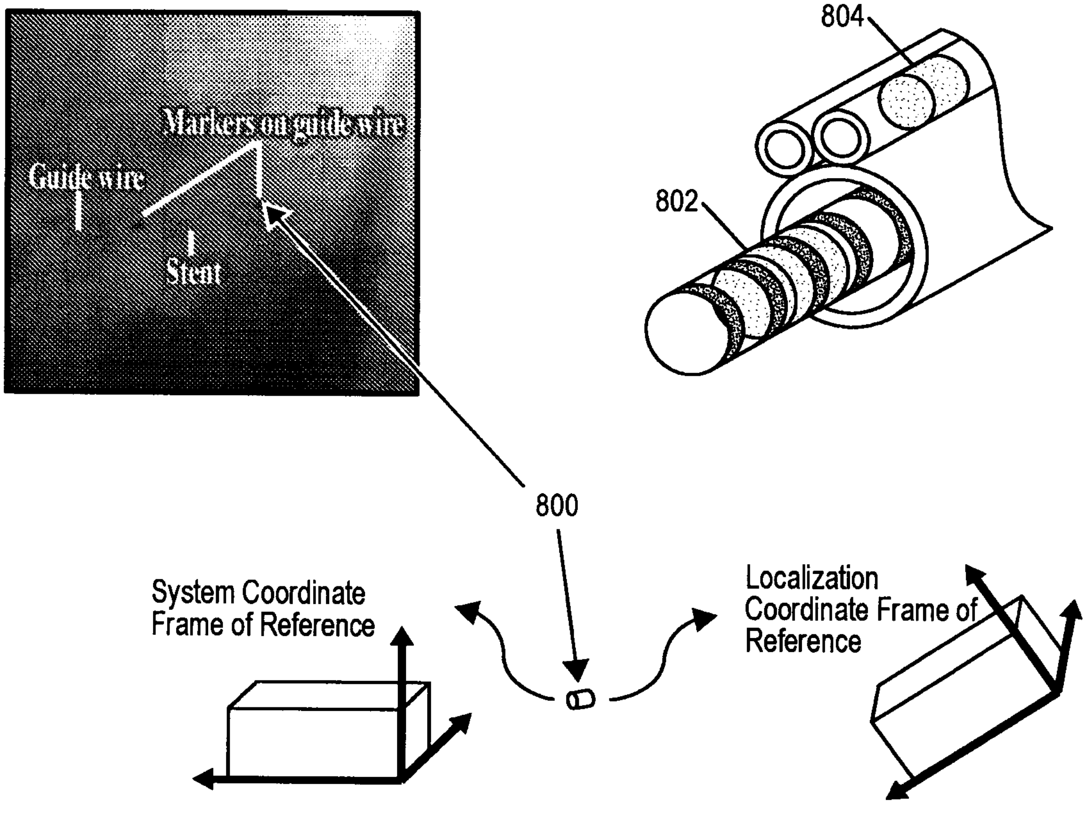
FIG. 8 is a diagram illustrating example coordinate frames of reference and registration of a device location within the coordinate frames.

As illustrated in FIG. 8, a system can optionally include a localization sensor/marker 800 (e.g., an imaging-visible marker) that can enable registration of a system coordinate frame of reference with a coordinate frame of reference of another modality. For example, localization markers/sensors 802, 804 can be included in the first and second flexible elongate instruments, each of which can be a marker 800 capable of appearing in an imaging modality, or one of which can be a marker 800 and the other of which can be detector capable of detecting the marker 800. In one example, the spatial encoding markers (or a position of the device as detected from the spatial encoding markers) can be spatially aligned with respect to one or more imaging-visible markers of the system. The spatial alignment can provide for registration (e.g., automatic registration) of a coordinate frame of reference of the system with an imaging frame of reference. In another example, the spatial encoding markers of the system (or a position of the device as detected from the spatial encoding markers) can be spatially aligned with a localization marker visible or otherwise detectable in another modality.

The alignment can be performed such that at least one of the first and second flexible elongate instruments is placed in a defined position and/or orientation in a complementary coordinate system, such as a coordinate system used in electromagnetic tracking/localization, ultrasound-based localization, or optical-shape-sensing-based localization. Upon alignment and registration of a portion of the device in both coordinate systems, position and orientation determinations by the system can be used to verify, refine, or augment spatial measurements obtained by the other modality.

While example systems and methods have been described with respect to the detectors being optical detectors and the stimulation energy being light, other types of detectors configured to detect other types of stimulation energy can be used.

Figure 10:
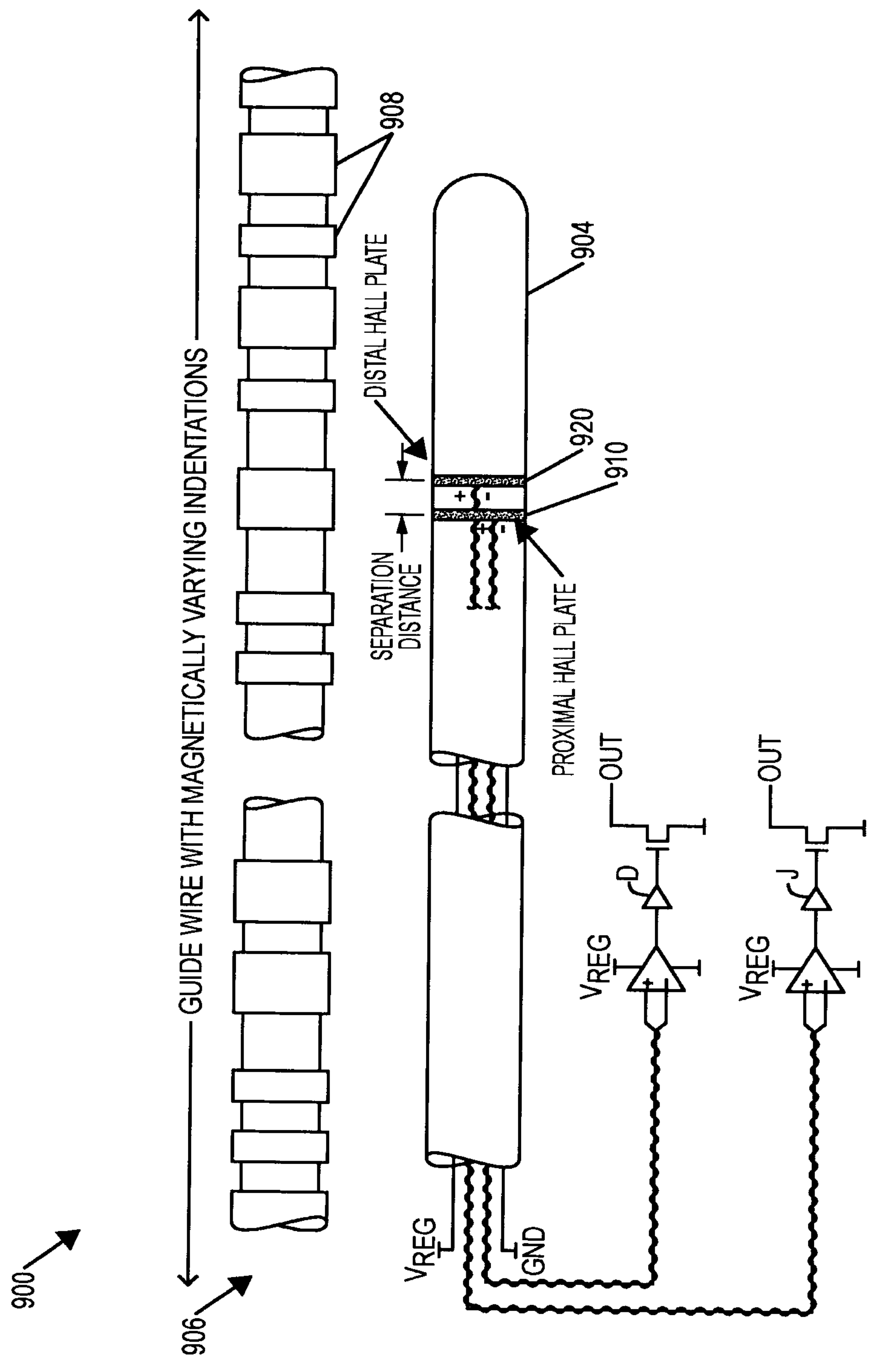
FIG. 10 is a schematic of a system having magnetic encodings and magnetic field detectors.

For example, a system in which magnetic encoding and magnetic detectors are used is shown in FIG. 10. The system 900 includes a first flexible elongate instrument 906 (e.g., as illustrated, a guidewire) and a second flexible elongate instrument 904 including two detectors 910, 920. The first flexible elongate instrument 906 includes a plurality of spatial encoding markers 908, which can be magnetically-varying indentations or magnetic rings disposed on the guidewire. The sensors of the detectors 910, 920 can be Hall effect plates. Hall effect sensors are generally known in the art. Each Hall effect plate can be supplied with a regulated voltage in one direction and can have signal output connection in a transverse direction, such that, when in a magnetic field, the Hall effect plate produces a voltage signal proportional to the magnetic field strength. In the example configuration shown in FIG. 10, an output voltage from each plate is further connected to a low noise amplifier, a Schottky buffer, and an open drain field effect transistor (FET) to complete a Hall effect sensor configuration. Such elements can be disposed at a location outside of the body lumen to provide for a minimal device profile for insertion. As the second flexible elongate instrument 904 is displaced relative to the first flexible elongate instrument 908, the detectors 910, 920 each obtain a signal from the spatial encoding markers 908, and a separation distance between each of the detectors 910, 920 can provide for an offset.

Returning to an example in which the system includes optical detectors, signal conditioning can be performed on the obtained signals. For example, the signal return from each optical detector can be the analog output from a photodiode optimized for reception of a desired wavelength (e.g., around 1310 nm). This signal can have digital attributes in that there are high amplitude regions when the sensor passes over a high reflective portion of the barcode, and a low amplitude when passes over a low reflective area of the encoding markers (alternatively referred to herein as a code track or barcode). The desired wavelength can be one that provides for low absorption losses in water or blood (e.g., 1310 nm).

It can be advantageous to treat this signal with an optimized SNR (signal-to-noise ratio). To achieve this, the signal can be conditioned to present a near full-scale value for A/D conversion. The first operation is to level shift the signal to remove its natural offset above zero volts. This can be achieved by a programmable subtractor circuit that can be adjusted to bring the minimum amplitude value of the signal to be near zero volts. The second operation is to either provide the necessary gain or attenuation to adjust the maximum amplitude of the signal to near the full-scale value of the conversion window.

Because of noise and signal strength variations of the signal, further processing can be split into two paths, as further described.

The first path is to continue to treat the signal as an analog signal and perform an A/D conversion on it. Software operations can be performed to create high and low thresholds. Above the high threshold the signal is treated as a logic '1', and below the low threshold a logic '0'. With the lead-lag nature of the 2-channel signal, the direction of movement can be determined; and, with the duration of the signal at a constant amplitude, its location within the pseudo-random serialized barcode and hence its position can be determined.

The second path is to treat the conditioned signals digitally and feed the signals into comparator inputs. The comparator outputs can preserve the lead-lag nature of the 2-channel detector, such that direction of movement can be determined. These digitized signals can be input directly into timer/counters permitting the duration of the signal at a constant amplitude to be precisely measured such that its location within the pseudo-random serialized barcode and hence its position can be determined.

These two paths can be complementary, as each can be used singly to achieve both a precise position and the direction of movement.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A system for measuring relative displacement between at least two flexible elongate instruments within a body lumen, comprising:
- a first flexible elongate instrument comprising a plurality of spatial encoding markers;
- a second flexible elongate instrument comprising two detectors, each detector comprising a single element sensor configured to obtain a signal from the spatial encoding markers, the single element sensor of one of the two detectors being offset from the single element sensor of the other of the two detectors, the first and second flexible elongate instruments configured for relative movement within a body lumen; and
- a controller configured to:
  - measure relative displacement of the first and second flexible elongate instruments based on the signals obtained from the two detectors and a detected offset of the obtained signals; and
  - determine a relative change in orientation between the first and second flexible elongate instruments based on the detected offset.

2. The system of claim 1, wherein the sensor offset is a longitudinal offset, an angular offset, or a combination thereof.

3. The system of claim 1, wherein the offset between the single element sensors is fixed.

4. The system of claim 1, wherein the controller is further configured to determine a relative direction of movement between the first and second flexible elongate instruments based on the detected offset.

5. The system of claim 1, wherein a position of the first flexible elongate instrument is fixed in a reference coordinate frame, and wherein the controller is further configured to determine an absolute position of the second flexible elongate instrument in the reference coordinate frame based on the detected offset of the signals obtained from the two detectors.

6. The system of claim 1, wherein the controller is further configured to determine an incremental change in position between the first and second flexible elongate instruments based on at least one of amplitude, frequency, phase, and timing variations between the obtained signals.

7. The system of claim 6, wherein the controller is further configured to translate the determined incremental change in position to an absolute position of one of the first and second flexible elongate instruments.

8. The system of claim 1, wherein the spatial encoding markers comprise a pattern that varies about a circumference of the first flexible elongate instrument.

9. The system of claim 1, wherein the at least two detectors are optical detectors, and wherein the single element sensor is a single element light sensor.

10. The system of claim 1, wherein the at least two detectors are magnetic field detectors, and wherein the single element sensor is a Hall effect plate.

11. The system of claim 1, wherein a stimulation energy source associated with at least one of the two detectors is configured to deliver pulsed energy or continuous energy.

12. The system of claim 1, wherein a stimulation energy source is associated with each of the two detectors, and wherein stimulation energy associated with one source varies with respect to stimulation energy associated with the other source in at least one of phase, timing, amplitude, and frequency.

13. The system of claim 1, further comprising a localization sensor or marker for spatial alignment of at least a subset of the encoding markers to a position defined in both a coordinate frame of reference of the system and a coordinate frame of reference of another modality.

14. The system of claim 13, wherein the localization marker is an imaging marker.

15. A multi-modality localization method, comprising:

with the system of claim 1, wherein the system further comprises a localization sensor or marker:

aligning one of the first and second flexible elongated instruments relative to the localization sensor or marker; and registering a position and orientation of the one of the first and second flexible elongated instruments based on a detected position and orientation of the localization sensor or marker in both a coordinate frame of reference of the system and a coordinate frame of reference of another modality.

16. The method of claim 15, further comprising:

updating a spatial measurement obtained from the other modality based on the measured relative displacement of the first and second flexible elongate instruments by the system.

17. The system of claim 1, wherein the sensor offset is configured to produce a lead-lag relationship between the signals obtained from the two detectors.

18. The system of claim 1, wherein the spatial encoding markers comprise one or more of non-uniform markers, pseudo-random markers, serialized markers, or code-character-based markers.

19. A method of measuring relative displacement between at least two flexible elongate instruments within a body lumen, comprising:

measuring relative displacement between a first flexible elongate instrument and a second flexible elongate instrument based on signals obtained from each of two detectors of the second flexible elongate instrument and a detected offset of the obtained signals, the first flexible elongate instrument comprising a plurality of spatial encoding markers, the second flexible elongate instrument comprising the two detectors, each detector comprising a single element sensor configured to obtain a signal from the spatial encoding markers, the single element sensor of one of the two detectors being offset from the single element sensor of the other of the two detectors, the first and second flexible elongate instruments being configured for relative movement within a body lumen; and determining a relative change in orientation between the first and second flexible elongate instruments based on the detected offset.

20. The method of claim 19, wherein the sensor offset is a longitudinal offset, an angular offset, or a combination thereof.

21. The method of claim 19, wherein the offset between the single element sensors is fixed.

22. The method of claim 19, further comprising determining a relative direction of movement between the first and second flexible elongate instruments based on the detected offset.

23. The method of claim 19, wherein a position of the first flexible elongate instrument is fixed in a reference coordinate frame, and wherein the method further comprises determining an absolute position of the second flexible elongate instrument in the reference coordinate frame based on the detected offset of the signals obtained from the two detectors.

24. The method of claim 19, wherein the method further comprises determining an incremental change in position between the first and second flexible elongate instruments based on at least one of amplitude, frequency, phase, and timing variations between the obtained signals.

25. The method of claim 24, wherein the method further comprises translating the determined incremental change in position to an absolute position of one of the first and second flexible elongate instruments.

26. The method of claim 19, wherein the spatial encoding markers comprise a pattern that varies about a circumference of the first flexible elongate instrument.

27. The method of claim 19, wherein the at least two detectors are optical detectors, and wherein the single element sensor is a single element light sensor.

28. The method of claim 19, wherein the at least two detectors are magnetic field detectors, and wherein the single element sensor is a Hall effect sensor.

29. The method of claim 19, wherein a stimulation energy source associated with at least one of the two detectors is configured to deliver pulsed energy or continuous energy.

30. The method of claim 19, wherein a stimulation energy source is associated with each of the two detectors, and wherein stimulation energy associated with one source varies with respect to stimulation energy associated with the other source in at least one of phase, timing, amplitude, and frequency.

31. The method of claim 19, further comprising:

aligning one of the first and second flexible elongated instruments relative to a localization sensor or marker; and registering a position and orientation of the one of the first and second flexible elongated instruments based on a detected position and orientation of the localization sensor or marker in both a coordinate frame of reference of the system and a coordinate frame of reference of another modality.

32. The method of claim 31, wherein the localization marker is an imaging marker.

* * * * *